United States Patent [19]
Birmingham et al.

[11] Patent Number: 5,989,824
[45] Date of Patent: Nov. 23, 1999

[54] APPARATUS AND METHOD FOR LYSING BACTERIAL SPORES TO FACILITATE THEIR IDENTIFICATION

[75] Inventors: Joseph G. Birmingham, Richland; Donald J. Hammerstrom, West Richland, both of Wash.

[73] Assignee: MesoSystems Technology, Inc., Richland, Wash.

[21] Appl. No.: 09/186,304

[22] Filed: Nov. 4, 1998

[51] Int. Cl.$^6$ .................................................. C12Q 1/68
[52] U.S. Cl. .................. 435/6; 435/287.2; 435/287.3; 435/287.9; 435/288.3; 435/288.5; 435/306.1; 313/48; 324/403
[58] Field of Search .................. 435/6, 287.2, 287.3, 435/287.9, 288.3, 288.5, 306.1; 313/48; 324/403

[56] References Cited

U.S. PATENT DOCUMENTS 4,954,320  9/1990  Birmingham et al. ............. 422/186.04

OTHER PUBLICATIONS

Bryden, Wayne A.; Benson, Richard C.; Ecelberger, Scott A.; Phillips, Terry E.; Cotter, Robert J.; and Fenselau, Catherine; "The Tiny–TOF Mass Spectrometer for Chemical and Biological Sensing,"John Hopkins APL Technical Digest, vol. 16, No. 3, 1995, pp. 296–310.

Bryden, Wayne A.; Benson, Richard C.; Ko, Harvey W.; and Donlon, Mildred; "Universal Agent Sensor for Counterproliferation Applications," John Hopkins APL Technical Digest, vol. 18, No. 2, 1997, pp. 302–308.

Carr, Anna K.; Roth, J. Reece; Brickman, C.; Kelly–Wintenberg, K.; and Montie, T.C.; "Killing Microorganisms in a Sealed Sterilization Bag with a One Atmosphere Uniform Glow Discharge," 4Q21, Abstract. Supported in part by the UTK Center for Materials, University of Tennessee. p. 231.

Hamilton, W. A. and Sale, A. J. H.; "Effects Of High Electric Fields On Microorganisms, II. Mechanism Of Action Of The Lethal Effect," Biochim. Biophys. Acta, I48, Jul. 1967, pp. 789–800.

Mizuno, Akira and Hori, Yuji; "Destruction of Living Cells by Pulsed High–Voltage Application," IEEE Transactions On Industry Applications, vol. 24, No. 3, May/Jun. 1988. pp. 387–394.

Mizuno, Akira; Inoue, Toru; Yamaguchi, Shigeo; Sakamoto, Ken–ichi; Saeki, Takakiyo; Matsumoto, Yoichi; and Minamiyama, Koichi; "Inactivation Of Viruses Using Pulsed High Electric Field," IEEE Transactions on Industry Applications, ©1990. pp. 77–83.

*Primary Examiner*—James Ketter
*Attorney, Agent, or Firm*—Ronald M. Anderson

[57] ABSTRACT

Bacteria cells and/or spores are collected and concentrated to form a specimen that is lysed using an ionized fluid to facilitate identification of the bacterial cells or spores by tests performed on the DNA and RNA contained therein. An impact collector is preferably used for separating the spores and cells from an air sample that is drawn through an input port of a portable housing. The resulting specimen is then exposed to an ionizing discharge that ruptures the surface membrane of the bacterial cells or spores. The ionizing discharge can be produced by a Tesla coil or other potential transformer that is electrically energized to produce an ionization potential, which is applied to an electrode, or to produce a corona glow discharge spread over a relatively larger surface of a plate-type electrode. Alternatively, air or another gaseous fluid in proximity to the electrode may be ionized by the ionizing potential or discharge from the electrode, forming an ionized fluid that is applied to the specimen. The surface membranes of the cells and/or spores are ruptured or cleaved by the ionizing discharge, exposing the nuclear DNA and RNA material contained therein. The lysed bacterial spores and/or cells are then processed by a cell RNA/DNA identifier, which uses a time of flight mass spectrometer or other assaying device to determine the types of spores and/or cells comprising the specimen. One preferred embodiment of the apparatus is housed in a portable housing and preferably includes a battery powered power supply, so that the apparatus is readily carried about in an adverse environment such as a battlefield to facilitate identification of bacteriological warfare agents.

32 Claims, 4 Drawing Sheets

5,989,824

APPARATUS AND METHOD FOR LYSING BACTERIAL SPORES TO FACILITATE THEIR IDENTIFICATION

FIELD OF THE INVENTION

The present invention generally relates to an apparatus and a method for lysing bacterial cells and spores, and more specifically, to apparatus and a method for cleaving the surface membranes of the cells and spores, exposing cell-nuclear material contained therein, to enable identification of the cells and spores.

BACKGROUND OF THE INVENTION

Bacterial cells and more particularly, bacterial spores, are able to survive in relatively adverse environments. The surface membranes of these organisms provide protection against harmful conditions. However, the surface membrane of a bacterial cell or spore comprises a shell protecting the deoxyribonucleic acid (DNA) and ribonucleic acid (RNA) contained therein that makes this material almost inaccessible for purposes of analysis and study. While it is possible to break down the surface membrane to expose the RNA and DNA of the spore with heat or by using chemical lysing agents, these techniques denature the cell-nuclear material so that the material is not of much use for analysis.

Examples of prior art techniques used for disrupting the surface membrane of bacteria cells (but not bacterial spores) include the use of a pulsed high voltage that creates a high voltage electric field. This electric field is capable of breaking down a bacterial cell wall, but has little effect on the surface membrane of bacterial spores. In a paper entitled, "Destruction of Living Cells by Pulsed High-Voltage Application," *IEEE Transactions on Industry Applications,* 24:3: May/June 1988, 387–394, Akira Mizuno and Yuji Hori report on the destruction of yeast cells (*Saccharomyces cerevisiae*) in a water solution using a high voltage pulse applied to electrodes exposed to the solution. The experiment was done with ionized water, and with a 1–3 percent NaCl solution in which the yeast cells were dispersed at a concentration of about $10^7$ cells/cm$^3$. High voltage pulses were applied to the solution N times (e.g., where N equals 175 times), and the pulses had a peak of either 12 kV or 20 kV, and a pulse width of about 90 to 160 $\mu$s. The survivability of the yeast cells decreased with increasing N. The high voltage pulse visibly destroyed some of the cells by puncturing their surface membranes, and destroyed others without any visible damage. The authors also postulate that some of the cells were destroyed by the shock wave resulting from application of the high voltage pulse to the solution. However, it appears that although many cells are killed using the high voltage pulse, and that some cell surface membranes are ruptured, the process does not assure that even a majority of the cell membranes will be punctured, exposing the DNA and RNA within the cells.

In a paper entitled, "Effects of High Electric Fields on Microorganisms," *Bicochim. Biophys. Acta,* 148, (1967), 789–800, W. A. Hamilton and J. H. Sale report on the effects of a series of high voltage direct current (DC) pulses of up to 30 kV/cm. on the membranes of *Escheria coli, Staphylococcus aureus, Bacillus cereus, Bacillus polymyxa* and other bacterial cells suspended in a 0.1 percent NaCl solution. It was noted by the authors of this paper that when *E. coli* were subjected to the DC pulse treatment, ninhydrin-positive material and 260-m$\mu$ absorbing material were found in the medium. Since amino acids, purine, and pyrimidine bases are characteristic of the intercellular contents, it is surmised that cell content leakage had resulted from this treatment. Furthermore, the authors reported that when suspensions of horse and bovine *erythrocytes* were treated with DC pulses, the turbidity of the suspensions decreased, which they believed resulted from the lysis of the *erythrocytes*. It was also shown that the treatment lysed protoplasts prepared from *M. lysodeikticus, S. ureae, B. subtilis*, and *B. megaterium*.

The prior art discussed above requires that the electric pulses be discharged into an aqueous solution in which bacteria cells are dispersed. It would be preferable to provide a technique for lysing bacteria cells that enables the cells to be concentrated and lysed in either a moist or dry environment. Further, it would be desirable to lyse substantially all of the spores exposed to the lysing medium, to improve the yield of cell-nuclear material for purposes of identification and analyses. Moreover, while the prior art teaches that an electric field can be employed to puncture bacterial cell surface membranes, it does not appear to indicate that an electric field is capable of lysing bacterial spore surface membranes. Clearly, it is desirable that any new technique usable for lysing should be capable of cleaving bacterial spores as well as bacterial cells.

One of the more important applications of technology requiring the lysing of bacterial cells and/or spores is in facilitating identification of biological agents that are used during bacteriological warfare or in attacks by terrorists. In order to permit known harmful bacteria to be identified, it is important that the DNA and RNA comprising the bacterial cells or spores found in the suspect environment be made available for analysis. By providing a reliable and portable apparatus for lysing bacteria cells or spores collected from the environment, it will be possible to identify bacteriological warfare agents in the field so that appropriate counteractive and protective measures can be implemented. A portable field monitoring device that includes the capability to collect, concentrate, lyse, and identify bacteriological warfare agents will greatly enhance the ability of civilian populations and troops to survive such attacks.

SUMMARY OF THE INVENTION

In accord with the present invention, a method is defined for lysing a cell, to expose nuclear material contained within a surface membrane of the cell. (It should be noted that for purposes of the claims that follow this specification, the terms "cell" or "cells" are respectively intended to include "spore" or "spores.") The claimed method includes the step of creating an ionizing discharge. A surface is provided on which a cell is disposed that is to be lysed or which has been lysed. The cell is then exposed to the ionizing discharge for at least a predefined interval of time, so that the ionizing discharge ruptures the surface membrane of the cell, exposing the nuclear material within the cell.

In a preferred form of the invention, the step of creating an ionizing discharge comprises the step of exposing an electrode to an ionizing potential. In one preferred embodiment, the cell is exposed to the ionizing discharge by directing the discharge toward the surface on which the cell is disposed. In an alternative preferred embodiment, the ionizing discharge is employed to ionize a fluid, producing an ionized fluid that ruptures the surface membrane of the cell. For example, air can be caused to flow adjacent to a member energized with an ionizing potential, thereby ionizing the air. The ionized air is then directed at the cell to cleave the surface membrane of the cell. As yet a further embodiment, the cell is conveyed past an ionizing discharge from an electrode that lyses the cell. The lysed cell is deposited on the surface.

In addition, the method may include the step of collecting a plurality of cells from an ambient environment by sampling the environment. The plurality of cells comprising this sample are then concentrated on the surface. After the cells in the sample are lysed, exposing cell nuclear material contained therein, the method may further include the step of identifying the cells by analyzing the nuclear material, to identify the type of cells in the sample.

Other steps of the method may include providing a bacterial cell collector, and using the bacterial cell collector to collect bacterial cells. These bacterial cells that are collected by the bacterial cell collector are deposited on the surface. It is also desirable that the method be implemented in a portable device, and include the step of activating the portable device to collect a sample of air from a surrounding environment so that any cells in the air are lysed to facilitate identification of the cells.

Another aspect of the present invention is directed to apparatus for lysing a cell in a manner that is generally consistent with the steps of the method described above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENTS

Figure 1:
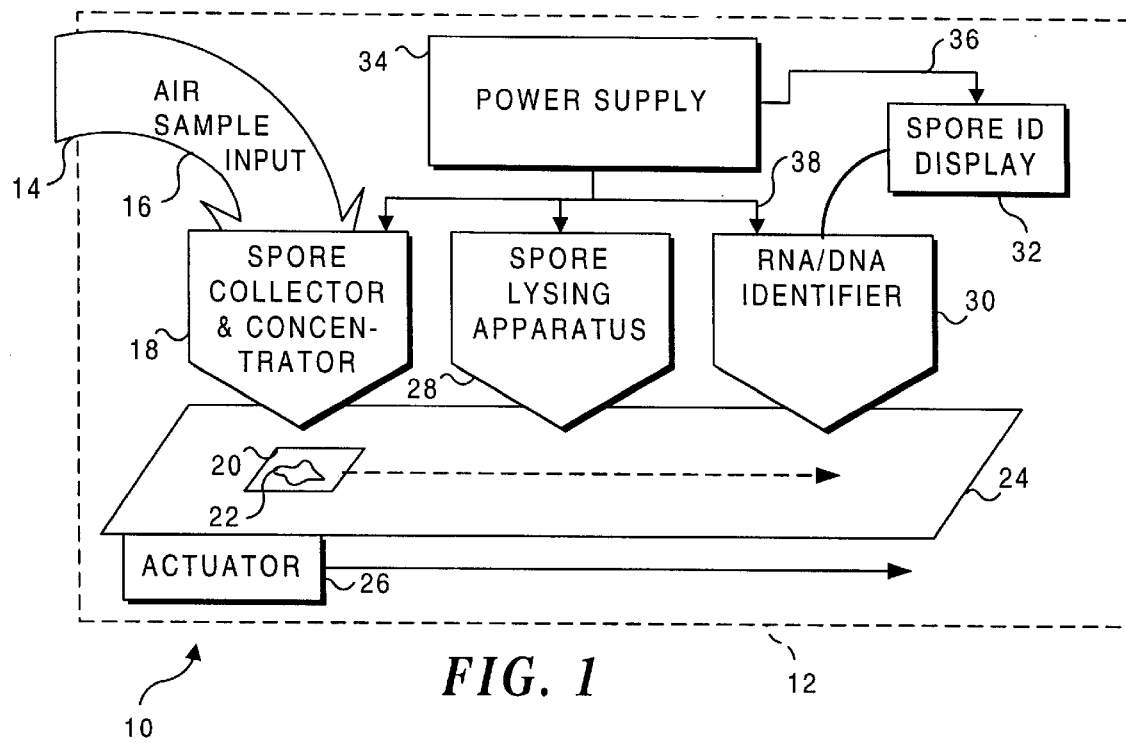
FIG. 1 is a functional schematic block diagram illustrating components of a system in accord with the present invention.

With reference to FIG. 1, an apparatus 10 suitable for practicing the present invention is schematically illustrated. It is expected that this apparatus be configured to fit within an enclosure 12 that is sufficiently small to be readily portable and carried about by an operator, suitable for possible use in a battlefield environment. In consideration of the conditions to which it may be exposed, housing 12 will provide protection for the components it encloses against temperature extremes and shock, but without adding undue weight or bulk. Housing 12 is thus preferably molded from an impact absorbing plastic that will provide these qualities.

An inlet 14 is disposed in housing 12 and provides a fluid path for an air sample 16 to be drawn into housing 12 and into a spore collector and concentrator 18. While this element is identified in the drawings as being useful for collecting and concentrating "spores," it will be appreciated that it is also useful for collecting and concentrating bacterial cells in addition to bacterial spores. In fact, apparatus 10 is intended to be used for collecting, concentrating, lysing, and identifying both bacterial cells and spores.

Preferably, spore collector and concentrator 18 comprises an impact collector in which spores and cells carried via air sample 16 through inlet 14 are separated from the air stream derived from the external environment surrounding housing 12. The bacterial spores and/or cells separated from the air stream are then deposited as a specimen 22 on a metal coupon 20 that is disposed adjacent to spore collector and concentrator 18.

While many other types of impacters are suitable for collecting spores and cells and concentrating them to produce specimen 22, a copending patent application entitled "Micro-Machine Virtual Impacter," U.S. patent application Ser. No. 08/880,355, filed on Aug. 6, 1997, discloses one design suitable for spore collector and concentrator 18. It is preferable that specimen 22 be disposed on the surface of metal coupon 20 in sufficient quantity to enable apparatus 10 to identify the type of bacterial cell and/or spore comprising the specimen. The purpose of apparatus 10 is to collect, concentrate, lyse, and identify bacterial cells and bacterial spores in the ambient environment surrounding housing 12, particularly bacterial cells and spores that have been released as bacteriological warfare agents. By facilitating the identification of such agents, appropriate steps can be taken to neutralize them and to protect personnel who might be exposed to the agents, from suffering adverse effects.

As the present invention is likely to be actually practiced, the sample of bacterial cells and/or spores that is collected from the environment will preferably be deposited on metal coupon 20, lysed, and the bacterial cells and/or spores identified without moving the coupon. However, for purposes of illustrating the serial nature of these steps, they are shown in FIG. 1 as occurring at three distinctly separate locations. Further, as shown in this Figure, it is contemplated that a belt or conveyer 24 can be employed to move coupon 20 with specimen 22 disposed thereon in the direction indicated by the dash line arrow. The belt or conveyer 24 is moved by an actuator 26, which comprises a prime mover such as an electric motor. (In one preliminary design of apparatus to implement the present invention, a video tape is used as a collection surface for the bacterial cells/spores and a suitable video tape drive is used for driving or moving the video tape; samples will be taken from the surrounding environment over a relatively long period of time, i.e., for several days.) Specimen 22 is preferably deposited on metal coupon 20 as a dry sample in which the bacterial cells and/or spores collected from the ambient environment are concentrated. Metal coupon 20 and specimen 22 are moved by conveyer 24 to a point adjacent a spore lysing apparatus 28. The spore lysing apparatus, which is configured in accord with the present invention, facilitates cleavage and rupturing of the surface membrane around each of the bacterial cells and/or spores comprising the specimen.

As noted above, it is important to expose the DNA and RNA comprising the nuclear material contained within the surface membrane of these bacterial spores and cells, without denaturing the material. Thus, spore lysing apparatus 28 does not use a chemical lysing agent or heat. Heat or a chemical lysing agent would tend to alter the nuclear material contained within each bacterial spore and/or cell, making the material virtually unusable for identifying the bacteria. It is not clear from the prior art that an electric field alone is able to lyse bacterial spores, although it would clearly assist in the lysing of bacterial cells.

Once the surface membranes of the bacterial cells and/or spores have been ruptured by lysing apparatus 28, the exposed nuclear material comprising specimen 22 is carried by conveyer 24 to a spore or cell RNA/DNA identifier 30. This identifier processes the nuclear material to identify the specific type of bacterial cells and/or spores comprising the specimen. The device preferably used for identifying the type of bacteria in the specimen is a time of flight mass spectrometer. However, a number of other types of bacterial spore and cell identifiers might alternatively be used. For example, identifier 30 may comprise a miniature flow cytometer, which determines bacterial type using fluorescent reagents. Or, a micro-fabricated device for biological detection analysis like that being developed by S. C. Jacobson of the Chemical and Analytical Sciences Division, Oakridge National Laboratory, can be used. The latter device employs electrokinetic manipulation of samples and reagents in microfabricated channels, and uses laser-induced fluorescence for detecting analytes.

Another type of sensor useful for identifying the bacterial spore and cell components of a specimen is a bio-aerosol fluorescence sensor like that being developed by T. Jays et al. in connection with the Massachusetts Institute of Technology and the U.S. Army, Edgewood Research and Development and Engineering Center, Aberdeen Proving Ground, Maryland. This device uses laser-induced fluorescence for detecting biological agents. Yet another alternative device is that being developed by Richard C. Ebersole, which employs immuno-PCR technology in which a toxin and viral antigens are detected using DNA-labeled antibodies that form a molecular complex with bound agents, which is then amplified via PCR so that internal sequences of the amplified products can be recognized. Still another type of identifying apparatus is a pyrolysis-gas chromatography-ion mobility spectrometer, which uses a chemical agent monitor for detecting specific spores or spore biomarkers.

It is contemplated that identifier 30 will be coupled to a spore or cell identification display 32 to provide a readout specifying each type of bacterial cell and spore identified through the assay or other determination carried out by identifier 30. It will be apparent that display 32 facilitates real time identification of bacterial spores and cells so that a relatively unsophisticated operator can employ apparatus 10, for example, in a battlefield environment or under other field conditions, to sample ambient air for purposes of identifying bacteriological agents.

A battery powered supply 34 is coupled to display 32 through leads 36 and to spore collector and concentrator 18, spore lysing apparatus 28, and spore RNA/DNA identifier 30 through leads 38. Although not shown, another lead couples the battery powered power supply to actuator 26 to provide electrical current for energizing its prime mover. For non-portable applications of the present invention, an alternating current (AC) line power supply can be used instead of battery powered supply 34.

Figure 2A:
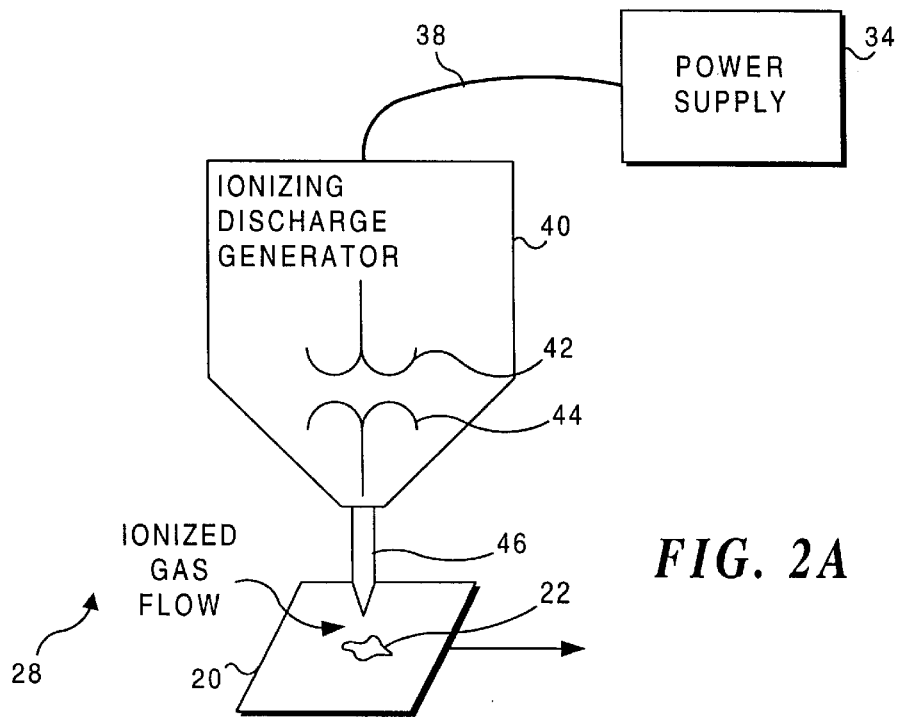
FIG. 2A is a schematic diagram showing details of a first embodiment of a cell or spore lysing apparatus included in the system of FIG. 1.

Further details of a first embodiment of a spore lysing apparatus 28 are shown in FIG. 2A. In this apparatus, an ionizing discharge generator comprising a Tesla coil 40 is provided that includes a primary winding 42 and a secondary winding 44. Primary winding 42 is connected through lead 38 to battery powered supply 34. Since the battery powered supply is a direct current (DC) source, it also includes a DC-to-AC converter (not specifically shown) for converting a DC voltage provided by a storage battery in the supply to an AC used for energizing primary winding 42 in Tesla coil 40. Note that if the power supply is AC powered, it will not require a DC-to-AC converter. In response to the electrical current flowing through primary winding 42, secondary winding 44 is excited to a relatively higher voltage. The turns ratio of primary winding 42 and secondary winding 44 is chosen so that an ionizing potential is developed on an electrode 46 that is connected to secondary winding 44. In this preferred embodiment, metal coupon 20 is at ground potential. The ionizing potential applied to electrode 46 produces an ionizing discharge directed to specimen 22 that ruptures the surface membranes of the bacterial cells and/or spores comprising the specimen.

Although not shown in the drawings, it has been determined that the ionizing potential can be applied to a plate-type barrier discharge electrode to produce a corona glow discharge over a relatively larger area The corona glow discharge thus produced can thus effect the rupture of bacterial cell and spore surface membranes of a sample covering a relatively larger area on metal coupon 20. This type of discharge comprises a more homogeneous glow discharge over the entire surface of the plate-type electrode. Other electrode configurations may also be used in accord with the present invention to apply the ionizing discharge to the specimen.

Figure 2B:
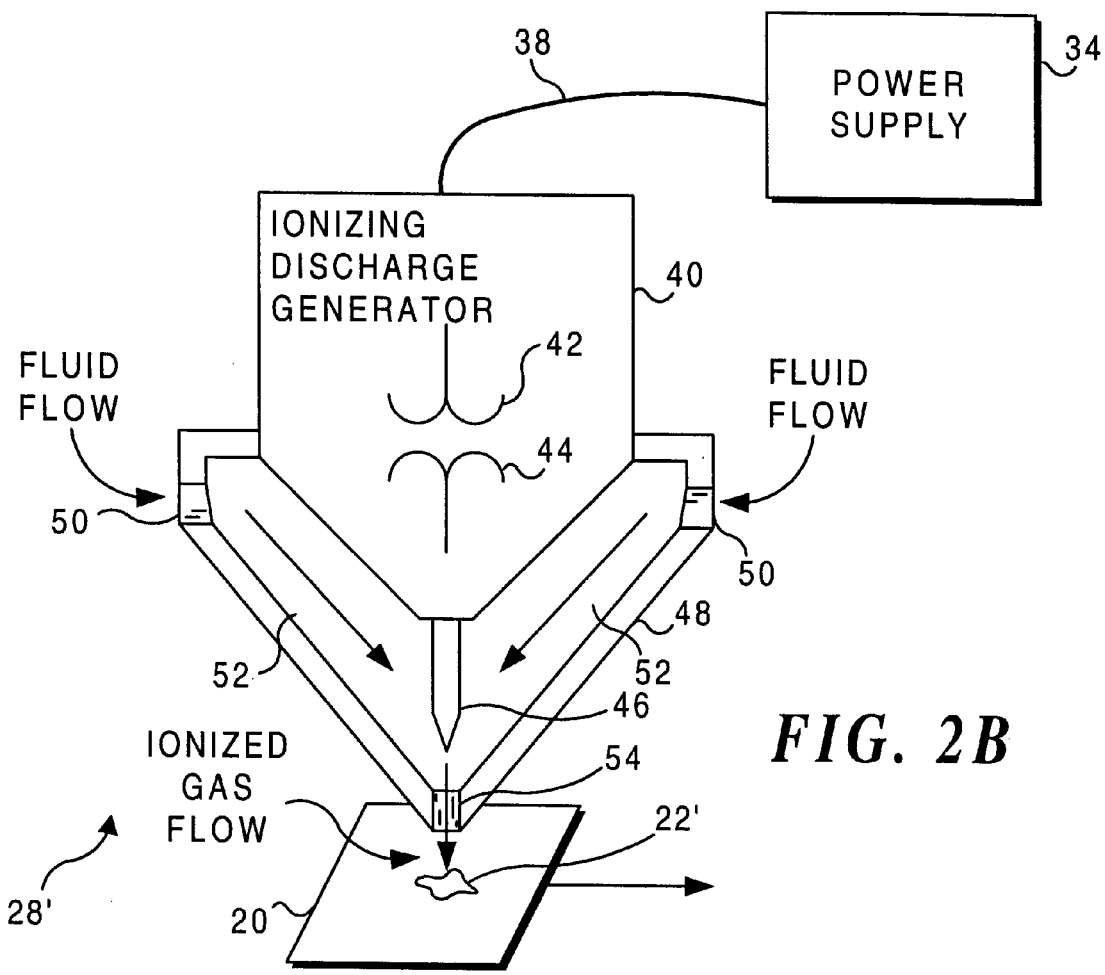
FIG. 2B is a schematic diagram showing details of a second embodiment of a cell or spore lysing apparatus included in the system of FIG. 1.

FIG. 2B illustrates a second embodiment of an ionizing discharge generator 28' that in one mode of operation also serves as a collector of the bacterial cells and/or spores. In this second embodiment, electrode 46 is disposed within a conical sleeve 48 that defines a chamber 52. Sleeve 48, which is coupled to ground potential, includes a plurality of inlets 50 through which air (or another gaseous fluid that is to be ionized) is introduced into chamber 52, either via a fan (not shown) or simply by ambient air pressure. The air or other fluid passing through inlets 50 flows around electrode 46.

In one mode of operation in which a separate spore collector and concentrator is not required, the air entering chamber 52 is drawn from the external environment and carries the bacterial cells and/or spores with it. When energized with an ionizing potential, electrode 46 produces an ionizing discharge that ruptures the surface membranes of the bacterial cells or spores carried by the air, lysing the bacterial organisms as they are carried by the air or other fluid through chamber 52. The lysed bacterial organisms are carried by the fluid through an outlet 54 and deposited as specimen 22' on metal coupon 20.

In a different mode of operation that uses separate spore collector and concentrator 18, the fluid entering chamber 52 does not carry the bacteria cells or spores. The ionizing potential applied to electrode 46 causes an ionizing discharge that ionizes the air or other fluid within chamber 52. It may be preferable to ionize a gas such as argon in chamber 52 instead of air, since argon is more readily ionized and is inert. The ionized air or other ionized fluid produced by the ionizing potential on electrode 46 exits conical sleeve 48 through outlet 54 that is disposed adjacent the specimen on metal coupon 20. Movement of the specimen past outlet 54 is controlled so that the specimen is exposed to the ionized fluid for at least 15 seconds (in the preferred embodiment), although the time required for completely lysing the bacteria cells and/or spores may depend upon the relative size of the specimen and other factors readily determinable by one of ordinary skill in the art. The ionized air or other ionized fluid exiting through outlet 54 ruptures or cleaves the surface membrane of bacterial cells and/or spores comprising the specimen, exposing the DNA and RNA nuclear material contained therein. This lysing process thus facilitates the identification of the specific type of bacterial cell or spore in the specimen by identifier 30.

Figure 3:
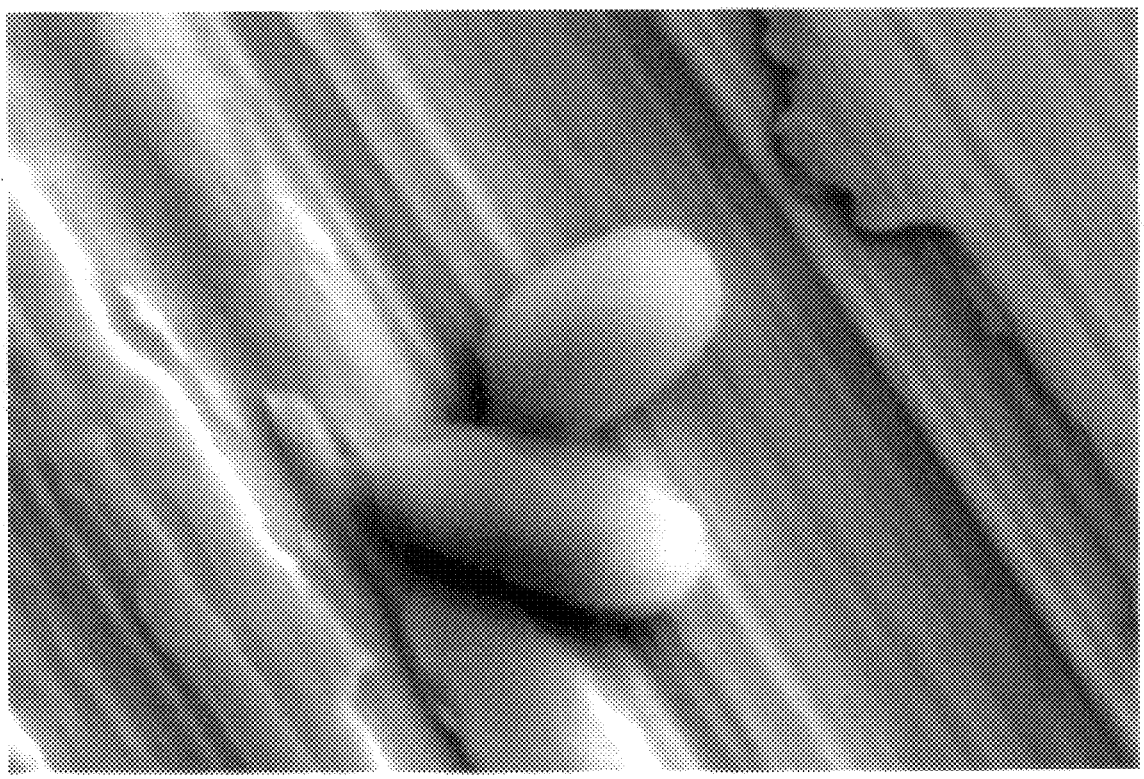
FIG. 3 is a photomicrograph (30,000 times magnification factor) of intact bacterial spores, *Bacillus globigi* (BG), as deposited on a metal coupon surface.
Figure 4:
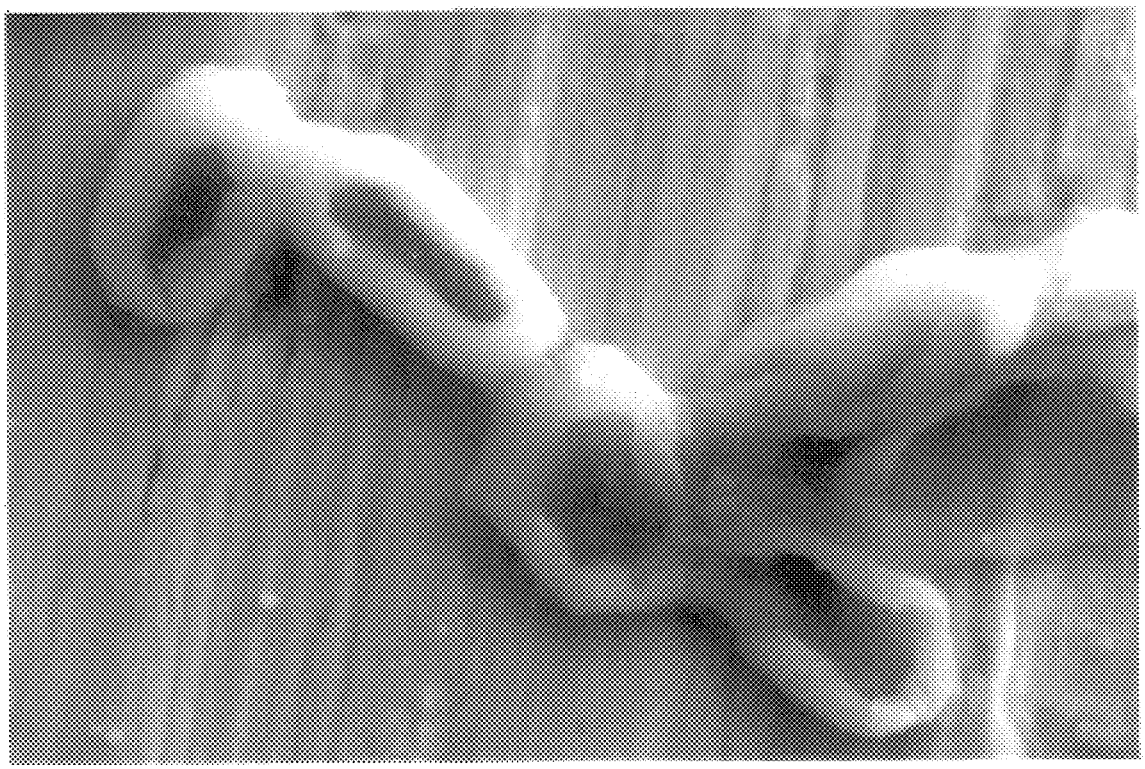
FIG. 4 is a photomicrograph of the BG bacterial spores (30,000 times magnification factor) after being exposed to ionized fluid for 15 seconds, showing the disruption of the surface membrane of the spores.

FIG. 3 is a scanning electron microscope (SEM) image at 30,000×magnification factor showing two intact BG spores 60. Intact BG spores 60 resist analysis using any of the above-noted techniques, because the surface membrane of the spores tends to protect the nuclear material contained therein. In contrast, lysed BG spores 62 shown in the SEM photomicrograph of FIG. 4, also made at 30,000× magnification factor, have been ruptured by an ionizing discharge so that their nuclear material is exposed. It will be apparent by comparing FIGS. 3 and 4 that the lysing apparatus comprising the present invention is very effective at rupturing or cleaving the surface membrane of bacterial spores, and thereby greatly facilitates the identification of the spores by identifier 30 (shown in FIG. 1).

Although the present invention has been described in connection with the preferred form of practicing it and modifications thereto, those of ordinary skill in the art will understand that many other modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for lysing a cell, to expose nuclear material contained within a surface membrane of the cell, comprising the steps of:
    (a) creating an ionizing discharge;
    (b) providing a surface on which the cell will be disposed either before or after the cell is lysed; and
    (c) exposing the cell to the ionizing discharge for at least a predefined interval of time, said ionizing discharge causing the surface membrane of the cell to be ruptured so that the nuclear material within the cell is exposed.

2. The method of claim 1, wherein the step of creating an ionizing discharge comprises the step of energizing an electrode with an ionizing potential, causing the ionizing discharge to occur from the electrode to another surface, so that the ionizing discharge affects the cell.

3. The method of claim 2, wherein the step of exposing the cell comprises the steps of employing the ionizing discharge to ionize a fluid; and, directing a flow of a resulting ionized fluid against the cell.

4. The method of claim 1, further comprising the steps of:
    (a) collecting a plurality of cells from an ambient environment by sampling the ambient environment;
    (b) concentrating the plurality of cells to produce a specimen; and
    (c) exposing the plurality of cells in the specimen to the ionizing discharge.

5. The method of claim 1, wherein the step of exposing comprises the step of moving a fluid in which the cell is disposed past a member to which an ionizing potential has been applied, the ionizing potential on said member creating the ionizing discharge to rupture the surface membrane of the cell, said cell with the ruptured surface membrane being collected on the surface.

6. The method of claim 1, wherein the step of exposing includes the step of exposing a fluid to the ionizing discharge to ionize the fluid and subjecting the cell disposed on the surface to the ionized fluid to rupture the surface membrane of the cell.

7. The method of claim 1, further comprising the steps of:
    (a) providing a bacterial cell collector;
    (b) using the bacterial cell collector to collect bacterial cells; and
    (c) subjecting the bacterial cells that were collected by the bacterial cell collector to the ionizing discharge to rupture surface membranes of the bacterial cells.

8. The method of claim 7, wherein steps (a) and (c) of claim 1 and steps (a)–(c) in claim 7 are carried out in a portable device, further comprising the step of activating the portable device to collect a sample of air from a surrounding environment.

9. A method for enabling cells to be identified, comprising the steps of:
    (a) collecting the cells and concentrating them to provide a sample;
    (b) creating an ionizing discharge;
    (c) exposing the cells in the sample to the ionizing discharge, for at least a predefined interval of time, interacting the ionizing discharge with the cells to lyse and rupture the surface membranes of the cells so that nuclear material within the cells is exposed; and
    (d) identifying the cells by analyzing the nuclear material that was exposed by interaction of the cells with the ionizing discharge.

10. The method of claim 9, wherein the step of collecting the cells comprises the step of taking a sample of a fluid that carries the cells from a surrounding environment.

11. The method of claim 9, wherein the step of creating the ionizing discharge comprises the step of applying an ionizing potential to a member, causing the member to produce the ionizing discharge.

12. The method of claim 9, her comprising the step of employing the ionizing discharge to produce an ionized fluid by moving a fluid past an element that is energized with an ionizing potential.

13. The method of claim 9, wherein the step of concentrating the cells comprises the step of separating the cells from a carrier fluid in which the cells are conveyed .

14. The method of claim 9, wherein the step of collecting and concentrating the cells deposits the sample on a surface that is exposed to an ionizing fluid produced by the ionizing discharge.

15. The method of claim 9, wherein the step of identifying the cells comprises the step of determining unique characteristics of the cells that are usable to identify the cells.

16. The method of claim 15, wherein the cells comprise bacterial spores.

17. Apparatus for lysing a cell to rupture a surface membrane of the cell, exposing cell nuclear material contained therein, said apparatus comprising:
    (a) a surface adapted to receive the cell, either after or before the cell is lysed; and
    (b) electrically powered means for lysing the surface membrane of the cell to rupture the surface membrane of the cell, exposing the nuclear material contained therein.

18. The apparatus of claim 17, wherein the cell is carried by a fluid sampled from an ambient environment.

19. The apparatus of claim 17, wherein the electrically powered means for lysing comprises a potential transformer that develops an ionizing potential.

20. The apparatus of claim 17, further comprising a housing for the surface and for the means for lysing, said housing being sufficiently compact to enable the apparatus to be readily portable and hand carried.

21. The apparatus of claim 17, further comprising a collector that samples a fluid carrying the cell and separates the cell from the fluid.

22. The apparatus of claim 21, further comprising an analyzer that identifies the cell by analyzing the cell nuclear material disposed on said surface after the surface membrane of the cell is lysed.

23. The apparatus of claim 22, wherein the electrically powered means for lysing includes a power supply.

24. The apparatus of claim 23, wherein the power supply includes a battery for providing electrical energy to energize the power supply.

25. The apparatus of claim 21, wherein the collector samples air from an external ambient environment, and separates cells carried by the air from a sample of the air.

26. Apparatus for enabling cells to be identified, comprising:
   (a) a collector that samples fluid from an environment that contains the cells and separates the cells from the fluid, producing a specimen;
   (b) an ionizing discharge generator, said ionizing discharge generator lysing the cells, rupturing their surface membranes and exposing nuclear material contained therein; and
   (c) an analyzer that identifies the cells by analyzing the nuclear material after the surface membranes of the cells are lysed.

27. The apparatus of claim 26, further comprising a power supply for energizing the collector, the ionizing discharge generator, and the analyzer.

28. The apparatus of claim 26, further comprising a housing that holds the collector, the ionizing discharge generator, and the analyzer.

29. The apparatus of claim 28, wherein the housing is portable, further comprising a battery power supply within the housing that provides an electrical current to energize the collector, the ionizing discharge generator, and the analyzer.

30. The apparatus of claim 26, wherein the ionizing discharge generator comprises:
   (a) a potential transformer;
   (b) an element coupled to the potential transformer, said potential transformer producing an ionizing potential that is applied to the element; and
   (c) means for exposing the cells to an effect of the ionizing potential.

31. The apparatus of claim 30, wherein the means for exposing the cells to the effect of the ionizing potential comprises a passage in which the element is disposed and through which a fluid conveying the cells, said cells being lysed by an ionizing discharge from the element.

32. The apparatus of claim 26, wherein the cells comprise bacterial spores.

* * * * *